US008881587B2

(12) United States Patent
Valenza, II et al.

(10) Patent No.: US 8,881,587 B2
(45) Date of Patent: Nov. 11, 2014

(54) GAS SORPTION ANALYSIS OF UNCONVENTIONAL ROCK SAMPLES

(75) Inventors: John J. Valenza, II, Melrose, MA (US); Nicholas J. Drenzek, Quincy, MA (US); Flora Marques, Paris (FR); Hendrik Grotheer, Bremen (DE); Dean M. Willberg, Tucson, AZ (US)

(73) Assignee: Schlumberger Technology Corporation, Sugar Land, TX (US)

( * ) Notice: Subject to any disclaimer, the term of this patent is extended or adjusted under 35 U.S.C. 154(b) by 417 days.

(21) Appl. No.: 13/359,121

(22) Filed: Jan. 26, 2012

(65) Prior Publication Data

US 2012/0192639 A1 Aug. 2, 2012

Related U.S. Application Data

(60) Provisional application No. 61/436,819, filed on Jan. 27, 2011.

(51) Int. Cl.
*E21B 49/02* (2006.01)
*G01N 15/08* (2006.01)

(52) U.S. Cl.
CPC ............ *G01N 15/088* (2013.01); *G01N 15/082* (2013.01); *G01N 2015/0866* (2013.01)
USPC ..................................................... 73/152.07

(58) Field of Classification Search
CPC .................... G01N 15/088; G01N 2015/0866; G01N 15/0893
USPC ..................................................... 73/152.07
See application file for complete search history.

(56) References Cited

U.S. PATENT DOCUMENTS

| | | | | |
|---|---|---|---|---|
| 3,349,625 A * | 10/1967 | Benusa et al. | ............... | 73/865.5 |
| 4,489,593 A * | 12/1984 | Pieters et al. | ..................... | 73/38 |
| 4,856,320 A * | 8/1989 | Bose et al. | ................... | 73/30.01 |
| 5,109,716 A * | 5/1992 | Ito et al. | ....................... | 73/865.5 |
| 5,239,482 A * | 8/1993 | Ajot et al. | ....................... | 702/30 |
| 5,342,580 A * | 8/1994 | Brenner | ......................... | 422/92 |
| 5,408,864 A * | 4/1995 | Wenman | .......................... | 73/38 |
| 5,482,524 A * | 1/1996 | Nakano et al. | ................ | 422/285 |
| 6,595,036 B1 * | 7/2003 | Nakai | .......................... | 73/19.05 |
| 7,140,231 B2 * | 11/2006 | Arii et al. | ....................... | 73/23.37 |
| 7,155,960 B2 * | 1/2007 | Arii et al. | ...................... | 73/31.05 |
| 7,429,358 B1 * | 9/2008 | Gross | ............................. | 422/83 |
| 8,505,375 B2 * | 8/2013 | Smalley | ..................... | 73/152.08 |
| 2002/0013687 A1 * | 1/2002 | Ortoleva | .......................... | 703/10 |
| 2003/0196810 A1 | 10/2003 | Vinegar et al. | | |
| 2004/0033557 A1 | 2/2004 | Scott et al. | | |
| 2004/0134258 A1 * | 7/2004 | Wang et al. | ........................ | 73/38 |
| 2005/0086997 A1 * | 4/2005 | Arii et al. | ..................... | 73/25.01 |
| 2008/0162056 A1 * | 7/2008 | Greaves | ......................... | 702/24 |
| 2009/0041629 A1 * | 2/2009 | Gross | ............................. | 422/69 |
| 2009/0254283 A1 | 10/2009 | Jacobi et al. | | |
| 2009/0260416 A1 * | 10/2009 | Coleman et al. | ............. | 73/19.01 |
| 2011/0030465 A1 * | 2/2011 | Smalley | ..................... | 73/152.07 |
| 2012/0217065 A1 * | 8/2012 | Gray | ............................... | 175/50 |
| 2013/0152665 A1 * | 6/2013 | Dunlop et al. | ............... | 73/19.09 |

* cited by examiner

*Primary Examiner* — John Fitzgerald
(74) *Attorney, Agent, or Firm* — Bridget Laffey; Wayne T. Kanak

(57) ABSTRACT

Systems and methods for gas sorption analysis, or analogous practices, of samples from unconventional reservoirs are described. The described analysis of samples is used to determine various properties of unconventional reservoirs, which are used in evaluating their worth and producibility.

2 Claims, 8 Drawing Sheets

GAS SORPTION ANALYSIS OF UNCONVENTIONAL ROCK SAMPLES

CROSS-REFERENCE TO RELATED APPLICATIONS

This application claims benefit under 35 U.S.C. 119(e) of U.S. Provisional Patent Application Ser. No. 61/436,819 filed on Jan. 27, 2011, which is incorporated herein by reference.

FIELD

This disclosed subject matter is generally related to gas shale formations, and more particularly to methods for accessing the maturity, free gas content, and transport characteristics or pore connectivity of gas shale formations.

BACKGROUND

A number of techniques exist for accessing organic matter (OM) maturity in shales. Rock-Eval pyrolysis is one of these techniques and consists of subjecting a small shale aliquot to a temperature cycle and monitoring the amount of gas-phase products evolving as a function of temperature. Typically, three generation events occur. The first event, S1, occurs as the sample is exposed to a temperature of 300° C. and consists of free hydrocarbons (gas and oil) that are volatilized. The second event, S2, occurs as the temperature increases to 550° C. at a rate of 25° C. per minute and consists of cracking non-volatile hydrocarbons, e.g. kerogen. The temperature at which this generation reaches a maximum, is called $T_{max}$, and may be interpreted as a measure of the shale maturity. $T_{max}$ may also be influenced by other OM characteristics, for example, initial composition and catalytic association with various minerals. Typical ranges of $T_{max}$ for immature are 400-430° C., mature 435° C.-450° C. and over-mature 450° C. A large proportion of gas shales are over-mature, but $T_{max}$ is relevant for assessing the degree to which the shale is over-mature. The third event, S3, is a measure of the amount of carbon dioxide that is associated with hydrocarbon cracking and S3 is useful for estimating the oxygen content of OM.

A second technique for assessing OM maturity consists of observing the percentage of light reflected from a shale sample, Ro %, where the percentage is calibrated against a standard that reflects 100% of the light. OM macerals become more glass-like and therefore reflect more light with increasing maturity. Typical ranges of Ro % are as follows: depositional (immature)—0.2-0.7; oil producing (immature-mature)—0.7-1.2 and gas producing (mature to over-mature) 1.2<Ro %<5.0. This technique was originally devised for determining the rank of coal and may be tedious, subjective, and imprecise. Moreover, due to the absence of vitrinite-producing land plants before ca. 360 million years ago, this technique cannot be applied to gas shales of older provenance.

A technique for measuring the free gas content consists of measuring the high pressure, high temperature methane capacity of a shale by fitting successive measurements of gas uptake as a function of pressure with a Langmuir isotherm to quantify total gas and adsorbed gas, where the difference is the free gas. In general, employing the Langmuir isotherm implies that analysis gas chemisorbs on the solid. However, methane does not chemisorb on the material constituents of shale. In this regard, information obtained by applying the Langmuir analysis may not be representative. Measuring the high pressure, high temperature methane capacity is time consuming, cumbersome and necessitates high pressure, for example, reservoir pressure, rendering it unattractive for applications at the wellsite.

SUMMARY

According to some embodiments, systems and methods of analyzing rock samples from an unconventional hydrocarbon reservoir are described. The methods include performing gas sorption on a sample of rock from the unconventional hydrocarbon reservoir; and determining at least one characteristic associated with the sample based at least in part on the gas sorption.

According to some other embodiments, a method for determining a location of a fracture zone for stimulation in a shale reservoir is described. The method includes obtaining a shale sample from the shale reservoir and grinding and sieving the shale sample. The method further includes degassing the shale sample and performing gas sorption on the shale sample from the shale reservoir to determine at least one characteristic associated with the shale sample based at least in part on the gas sorption. Finally, the method includes determining the fracture zone from the one or more characteristics.

According to some embodiments, a method of analyzing a rock sample is described. The method includes obtaining the rock sample and measuring a pore volume or porosity on a plurality of particles of varying sizes from the rock sample. The method further includes, comparing the measured pore volume or porosity to determine a correlation length or pore connectivity in the rock sample.

As used herein the term "unconventional" reservoir includes reservoirs having an unconventional microstructure, such as having submicron pore size, and/or substantial amounts of primary organic matter such as kerogen. Examples of unconventional reservoirs include hydrocarbon-bearing shales such as gas shales and oily shales.

Further features and advantages of the invention will become more readily apparent from the following detailed description when taken in conjunction with the accompanying drawings.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION

Figure 1:
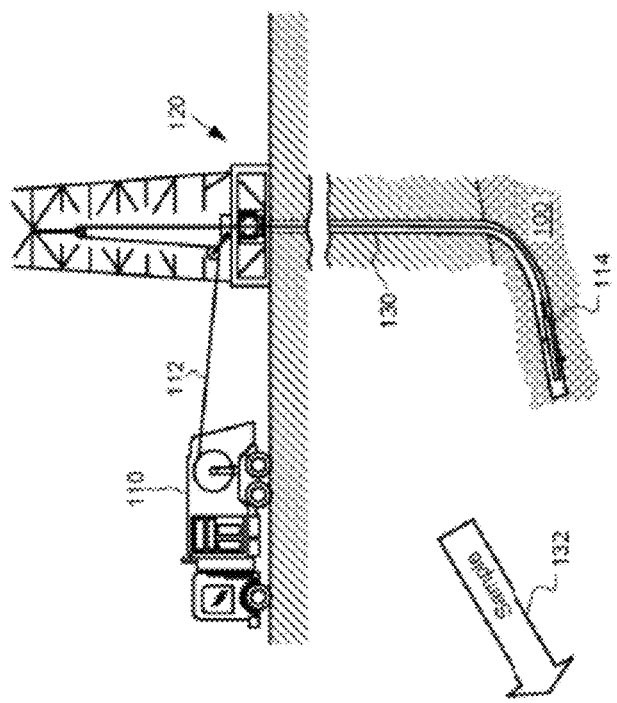
FIG. 1 shows a sampling tool being deployed in a wellbore and an analysis facility, according to some embodiments.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice. Further, like reference numbers and designations in the various drawings indicate like elements.

In embodiments, methods are disclosed for accessing the quality of a shale reservoir. The information derived from the methods disclosed may be utilized for completion design. Stimulation is the most costly process (in general at least 50% of a well cost) utilized for gas shale plays so gaining insight into the location of the best zones for stimulation is important. These include zones with the most mature organic matter as mature organic matter contains oil-wet pores which may represent unimpeded pathways to the fractures formed during stimulation. Generally, the gas in shale is in one of two states which are (a) tightly absorbed on the rock surface (liquid-like) or (b) free in the body of the pores (gas-like). Laboratory measurements indicate that initially the free-gas is produced and the adsorbed gas is produced when the reservoir pressure is reduced. It is therefore an advantage to identify mature zones with the greatest proportion of free gas.

The subject disclosure utilizes conventional gas sorption for characterizing the microstructure of gas shale. Gas sorption is applicable for characterizing nanoporosity (<200 nm) and therefore is an ideal technique for characterizing the microstructure of gas shale. In a non-limiting example a gas sorption study is performed at the boiling point of the analysis gas (−196° C. for nitrogen). Under these conditions the saturation vapor pressure, $P_0$, of the analysis gas is equivalent to ambient pressure (~0.1 MPa). Other analysis gases which may be used include argon, xenon, neon or any molecular or atomic probe known to be useful in adsorption studies. The disclosure implicitly covers the normal thermodynamic conditions with respect to range of temperature and pressure, regularly imposed for the various analysis gases. Experiments consist of measuring the volume of adsorbed gas, $V_A$, from low (~1 kPa) to ambient pressure at constant temperature (commonly referred to as an isotherm). At the low end of the pressure range, gas molecules stack in multiple layers on the internal surfaces of the shale, permitting determination of surface area $A_S$. At higher pressure, liquid nitrogen condenses in the fine pores of the shale, permitting determination of the pore size distribution for pores smaller than 200 nm, and the pore volume $V_p$.

FIG. 1 shows a sampling tool being deployed in a wellbore and an analysis facility, according to some embodiments. In a non-limiting example the sampling tool is a core sampling tool. Wireline truck 110 is deploying wireline cable 112 into well 130 via well head 120. Wireline tool 114 is disposed on the end of the cable 112 in an unconventional subterranean formation 100. According to some embodiments, formation 100 is an unconventional reservoir, such as a hydrocarbon bearing shale reservoir. Tool 114 includes a sampling tool as shown, in a non-limiting example a core sampling tool. Although a wireline sampling tool is shown, according to other embodiments, other types of sampling tools are used such as while drilling and/or coiled tubing conveyed tools. Samples 132 are from an unconventional rock formation 100 and are retrieved at the surface from the tool 114 and transported to an analysis facility 160. Note that the analysis facility 160 can be located at the wellsite (which can be onshore or offshore) or it can be located remotely from the wellsite. Facility 160 includes a gas sorption apparatus (152), one or more central processing units 140, storage system 144, communications and input/output modules 140, a user display 146 and a user input system 148. Input/output modules 140 include modules to communicate with and control the gas sorption machine (152). Facility 160 may also include a helium pycnometry (He-pyc), mercury intrusion porosimetry (MICP) or other apparatuses as known to those skilled in the art for characterizing rock samples.

By using conventional gas sorption it can be shown that the microstructural characteristics of shale are dependent on the shale maturity. The correlation between the microstructure and maturity is due to pores which form in the organic matter as hydrocarbons are generated and ultimately expelled. These pores are characterized by length scales that range from $10^{-9}$-$10^{-7}$ m. The high surface to volume ratio of these nanopores is responsible for an increase in specific area, $A_s$, with maturity. An increase in maturity leads to a concomitant increase in porosity and surface area due to nanometric pores in the total organic content. These pores increase pore connectivity and are formed as a result of hydrocarbon generation and expulsion. This increase in specific area, $A_s$, with maturity is depicted in FIG. 2.

Figure 2:
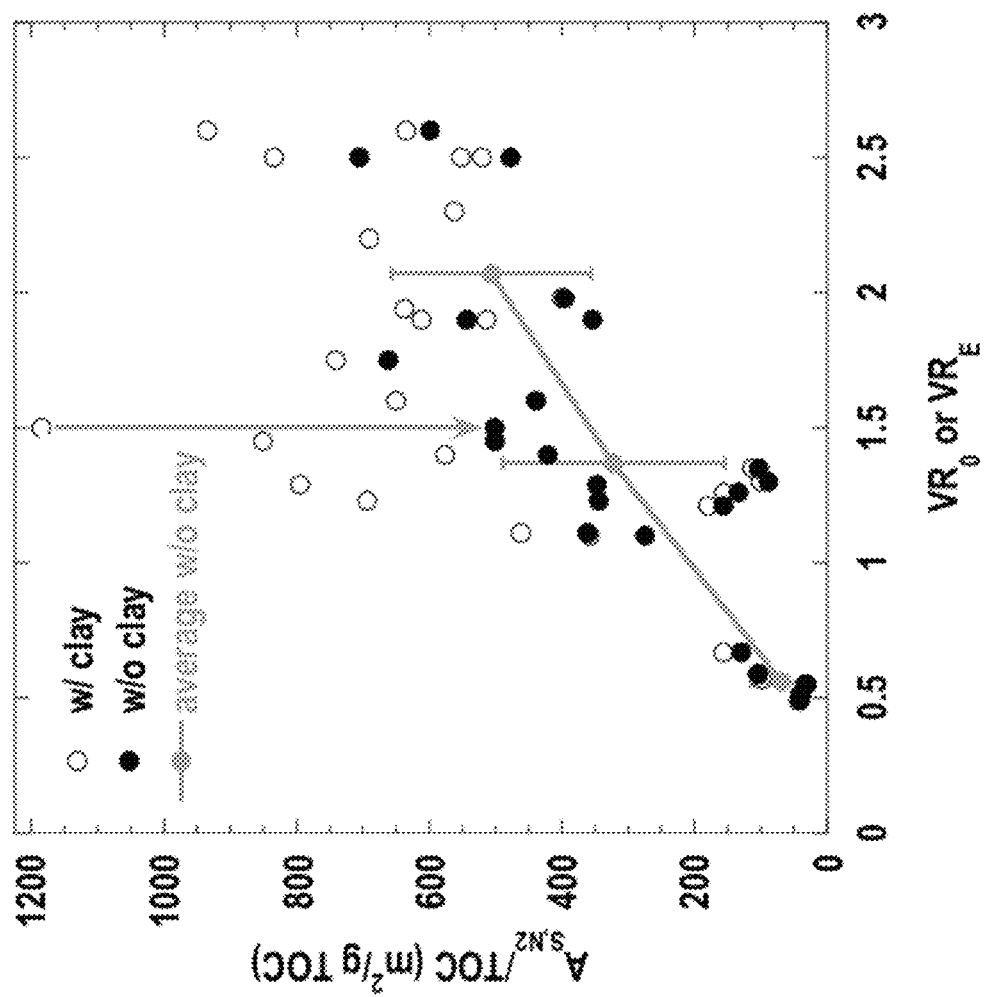
FIG. 2 is a plot of $A_{S,N2}$ normalized by total organic content (TOC) versus vitrinite reflectance ($VR_O$) or the bitumen equivalent ($VR_E$)

FIG. 2 is a plot of $A_{s,N2}$ normalized by TOC versus virtinite reflectance ($VR_O$) or the bitumen equivalent ($VR_E$). Thermal maturity is indicated by vitrinite reflectance, $VR_O$, or the equivalent determined on bitumen, $VR_E$ (for higher maturity), which are acquired by standard organic petrology. A similar related metric commonly used is Tmax. The plot shows that the surface area increases with maturity. The open circles are the raw data, while the filled surfaces show the surface area attributed to organic matter alone. Since $A_{s,N2}$ represents that due to organic and clay (open symbols), there is considerable scatter in the data, especially in the samples that are moderately mature. Therefore, $A_{s,N2}$/TOC is reduced by an amount attributable to clay (filled symbols). The proportion of $A_{s,N2}$ attributable to clay is given by the XRD mineralogy, the relationship displayed in Equation 1 (free exponent) below for the proportion of clay accessible to the analysis gas, and G the ratio of the surface area of pure clay as measured by nitrogen to that measured by water.

$$A_{S,N2}(\text{no clay}) = A_{S,N2}(\text{with clay}) - B*(I+S)*G*\left(\frac{TOC}{100}\right)^{-0.998} \quad \text{Equation 1}$$

As can be seen in FIG. 2 the specific surface area of the organic matter (filled symbols) increases markedly over the spectrum of maturity investigated. Mature ($VR_O$>2) TOC has a specific surface area of 400-600 m²/g which is consistent with previously published values from artificially matured shale, and is similar to that of activated carbon. The plot also shows the average $A_{s,N2}$ from samples with 1<$VR_{O\ or\ E}$ (immature), 1<$VR_{O\ or\ E}$<1.5 (moderate) and 1.5<$VR_{O\ or\ E}$ (mature). The average value for mature shale is more than an order of magnitude greater than that for immature shale, and nearly twice that of moderately mature shale.

Figure 3:
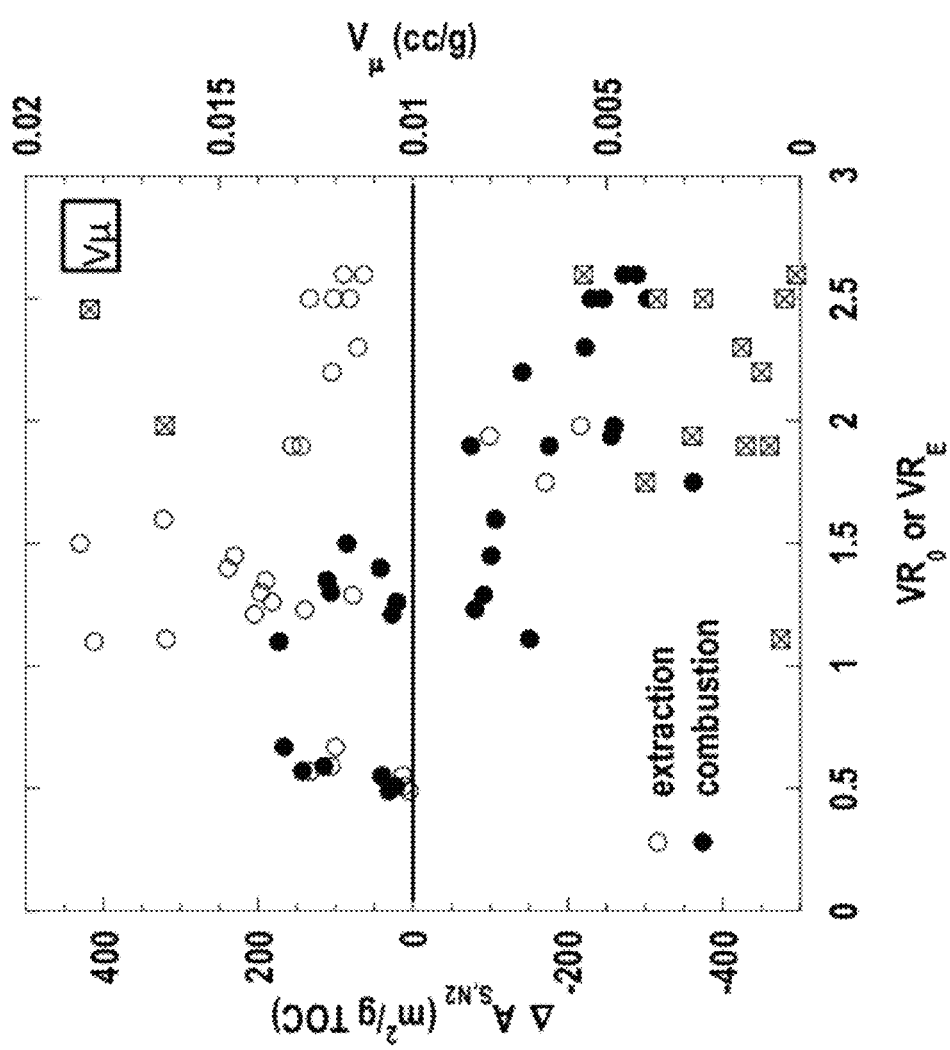
FIG. 3 is a plot of the change in surface area after bitumen extraction and combustion as a function of $VR_O$ or $VR_E$.
Figure 4:
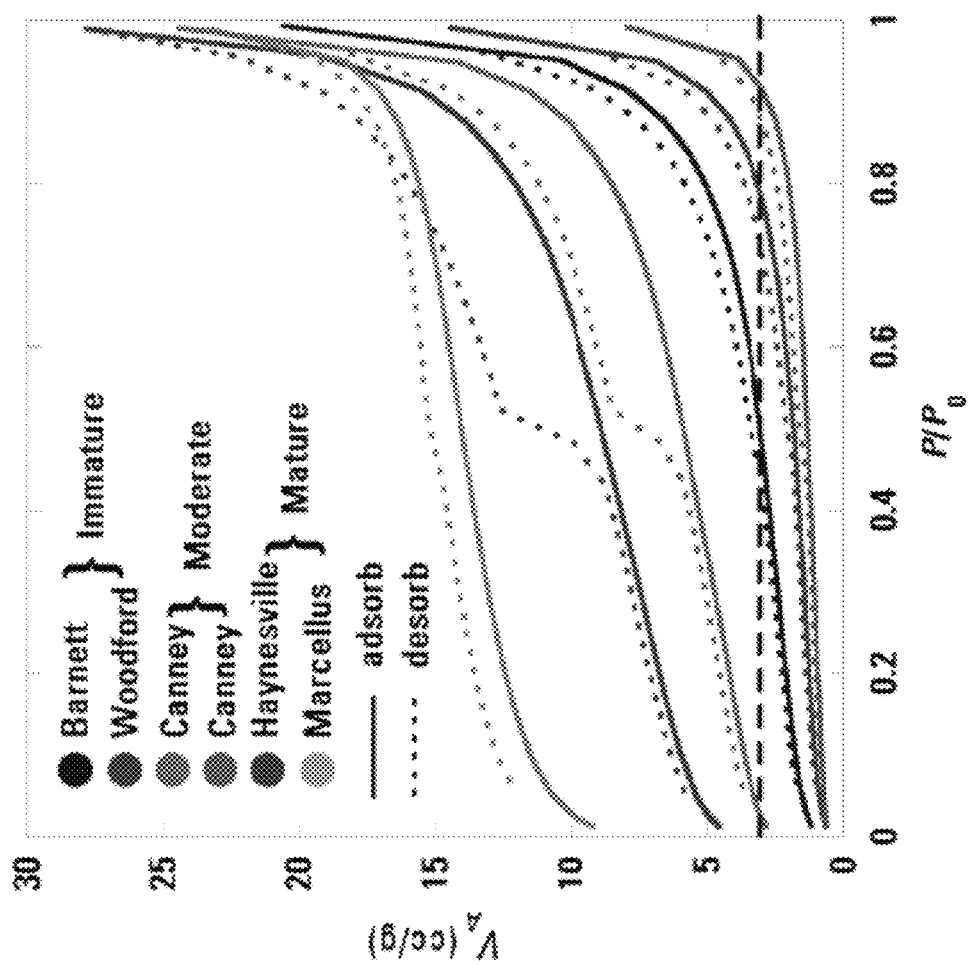
FIG. 4 is a plot of isotherms for shale of varying maturity.

Further, it has been found that micropores (pore size <2 nm as defined by the International Union of Pure and Applied Chemistry (IUPAC)) are found in moderate to highly mature shale as depicted in FIG. 3. FIG. 3 is a plot showing the change in surface area after bitumen extraction, and combustion as a function of $VR_O$ or $VR_E$. Also shown is the volume of micropores Vμ determined using, in a non-limiting example, the t-plot analysis on gas sorption data from the as received material. Vμ could also be measured directly by performing gas sorption with carbon dioxide. The high specific surface area of the kerogen is due to the increase in nanoporosity, including Vμ, with maturity. These extremely small micropores (<2 nm) absorb a high volume of gas at low pressure and this may be used for identifying mature zones by simply measuring the amount of gas adsorbed at very low pressure ($P/P_0$<0.05), as depicted in FIG. 4. FIG. 4 is a graph of isotherms for shale of varying maturity. The presence of micropores elevates $V_A(P/P_0 \to 0)$ in the mature shale. This observation provides a rapid maturity index. The horizontal dashed line in FIG. 4 is an example of a lower bound on $V_A(P/P_0 \to 0)$ above which a sample would be considered mature.

Further, adsorbed gas ($V_A$) is measured for a plurality of increments, in a non-limiting example, seven increments of pressure up to $P_0$, where the last data is taken at $P/P_0 \sim 0.995$. $V_A(P/P_0 \to 0)$ (e.g. maturity), $A_S$ (surface area), and $V_P$ (pore volume) can then be determined from this information. The latter two quantities may be combined to provide an estimate of the pore volume available to free gas, $V_F$, given the thickness of the layer of natural gas adsorbed in practice, $t \sim 1$ nm; $V_F = V_P - A_S t$. Moreover, these quantities can be utilized to estimate the total gas in place or hydrogen index given the reservoir pressure and the associated gas density profile in the pore (e.g. higher density in the adsorbed phase near the pore wall, decaying to bulk density in the center of the pore.). In a non-limiting example the Brunauer, Emmet and Teller analysis (BET) is utilized to determine, $A_s$ given $V_A$ at several pressures below $P/P_0$<0.3. BET is a statistical analysis of the buildup of gas multilayer's on a solid surface. The primary result is an expression for the number of gas molecules in a monolayer. In a non-limiting example, the t-plot technique is used to determine the volume of micropores, Vμ, given $V_A$ over the entire range of pressure. This approach utilizes a transformation of variables between P and the thickness of adsorbed gas, $t_A$, to deduce Vμ, where the transformation of variables is determined on a chemically similar non-porous sample. The idea is that if $V_\mu = 0$, a plot of $V_A$ versus $t_A$ passes through the origin.

Figure 5:
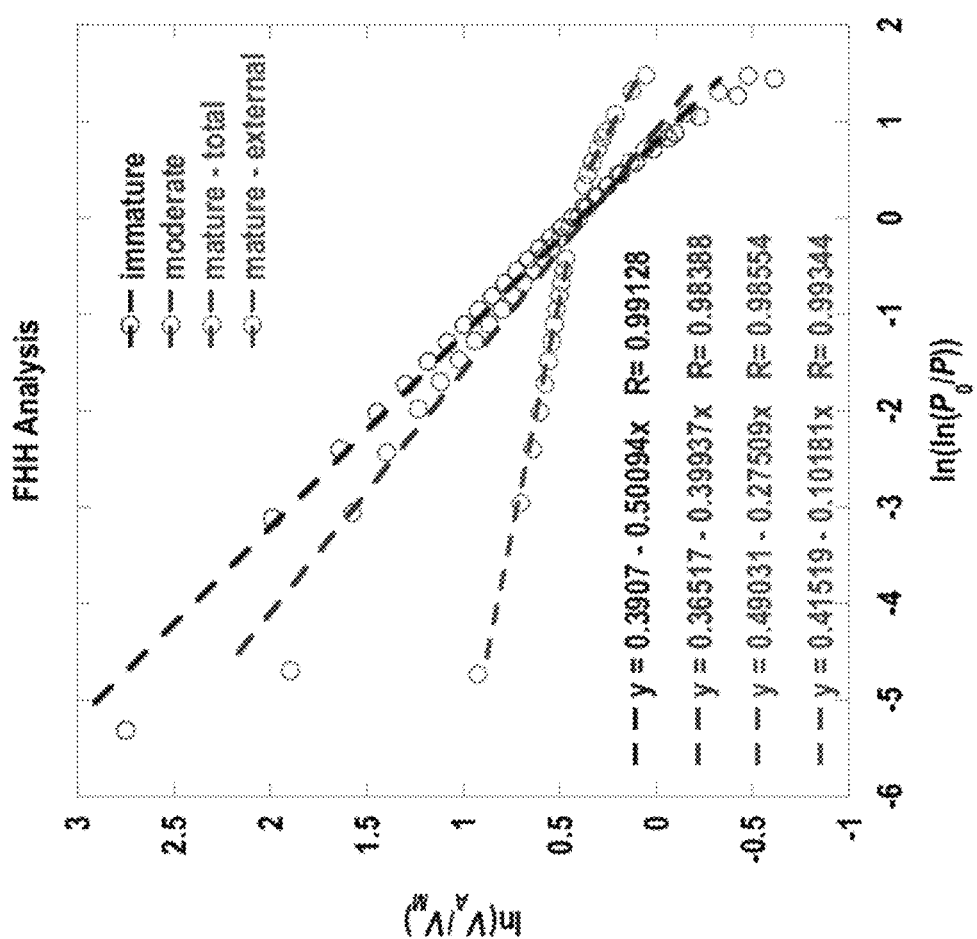
FIG. 5 is a plot of the natural log of $V_A$, normalized by $V_M$ from BET analysis, versus the double natural log of $P/P_0$.

Shale is a fractal material, and as such access to the microstructure is described by percolation concepts. FIG. 5A is a plot of the natural log of $V_A$, normalized by $V_M$ from BET analysis, versus the double natural log of $P/P_0$. The plot is linear over nearly two orders of magnitude in pressure, which corresponds to nearly two orders of magnitude in pore size. The slope of the line, m, gives the fractal dimension $D_F = m + 3$. $D_F$ increases with maturity, indicating that at a given characteristic length, a greater pore volume is accessible with increasing maturity.

Figure 6:
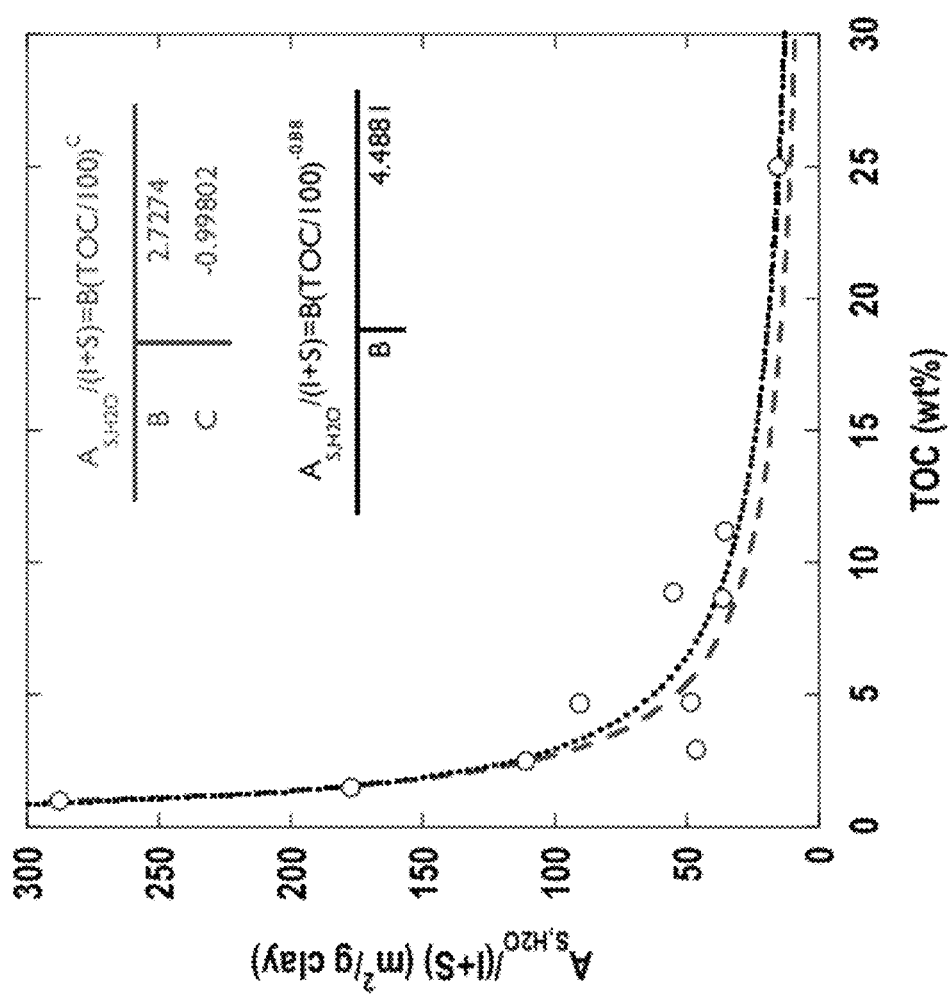
FIG. 6 shows sorption results using water vapor as the analysis gas, $A_{S,H2O}$, normalized by the mass of illite+smectite (I+S) in the sample.

Shales are distinguished from conventional reservoir rock by their more abundant clay and OM content. $A_{s, H2O}$ normalized by the mass of illite and smectite (I+S) exhibits a power law dependence on TOC. FIG. 6 plots $A_{s, H2O}$ normalized by the mass of illite and smectite (I+S) versus TOC. The data corresponds to a number of samples across the spectrum of maturity. As can be seen in FIG. 6 there are two power law fits to the $A_{s, H2O}/(I+S)$ data, one with the exponent as a free parameter (gray) and the other with the exponent fixed (black). Water vapor is used as it will not condense on organic surfaces. Therefore, $A_{s, H2O}$ inferred from these measurements is indicative of that due to exposed inorganic surfaces. In shale, inorganic surface area is dominated by clay, where the specific surface area of clay as measured by water is $A_{s, H2O} \approx 300-400$ m²/g. Normalizing $A_{s, H2O}$ by the total clay content of the sample (I+S=Illite+Smectite) as determined by x-ray diffraction, the resulting value is strongly correlated to TOC, and that in the limit of TOC→0, the value $A_{s, H2O}/(I+S)$ is consistent with the specific surface area of clay. These results are very useful because they yield several key insights. First, the power law fit to the data in FIG. 6 has an exponent that is similar to that for 3D conductivity in the system. This is important because it is indicative that percolation concepts apply for gauging access to the porosity. Moreover, the TOC in the mature systems contributes numerous pores which provide access to the porosity which yields access to the inorganic surfaces. Applying percolation concepts, we expect the correlation length (χ) to vary with a similar power law, $\chi = \chi_0 (p - p_C)^{-\nu}$, where ν=0.88 for 3D percolation, $\chi_0$ is a fundamental length, like the characteristic dimension of the organic matter, and p is the volume fraction of a component in the sample, in this case TOC. Since we use a consistent particle size in our experiments, we conclude that the relative correlation length decreases with TOC content, or a reduction in maturity. For the oilfield this information is useful because smaller χ necessitates greater stimulation to access the natural resource trapped inside the rock. Of course, the correlation length can also be determined by running the gas sorption measurement on a single sample by varying the particle size used in the analysis. This will give the discrete range of particle sizes in which χ lies (e.g., bounded below by the largest particle size which yields a consistent $A_S$, and above by the first particle size which yields lower $A_S$).

Embodiments of the subject disclosure comprise techniques for characterizing shale using gas sorption. The permeability of shale is very low ($10^{-19}$-$10^{-20}$ m²) so the particle size is reduced (0.001-10 mm) so the gas molecules may probe the pore network rapidly. To achieve low pressure, samples are degassed before running experiments.

According to some embodiments a shale sample is retrieved and the sample is grinded and then sieved ensuring all material passes through a sieve with 150 μm openings. According to some embodiments the sample size is on the order of 1 g. The sample is then loaded into an analysis tube and the mass of the sample is noted. The analysis tube is then loaded onto an analyzer to degas. Gas sorption analysis is then performed. $V_A$ is noted for a plurality of $P/P_0$ in the pressure range 0.001<$P/P_0$<0.995. This includes a point very near the upper bound. $V_A$ is also noted in the limit, $P/P_0 \to 0$. The sample is determined to be mature or not by comparing to lower bound for mature samples: $V_A(P/P_0 \to 0)$=3-4 cc/g, see also FIG. 4. If the sample is mature, a t-plot analysis may be used to determine $A_s$ and the volume of micropores, otherwise a BET analysis may be used to determine $A_s$. The pore volume ($V_P$) may be noted from $P/P_0$ and the pore volume available to free gas ($V_F$), and the gas in place or hydrogen index may also be determined as indicated above.

According to some embodiments the particle size may be varied to quantify the associated effect on access to the porosity. If the particle size is varied over a broad enough range, the data will provide insight into the correlation length of the shale and the total pore volume or porosity.

According to some embodiments the particle size may be varied and helium pycnometry (He-pyc), mercury intrusion porosimetry (MICP), or other techniques as known to those skilled in the art for measuring pore volume or porosity are used to yield information and also to determine the correlation length of shale. He-pyc determines the volume of solids in a sample of known mass, by allowing a known amount of Helium gas to expand into a container of known volume that holds the sample of interest. The volume of solids is given by the equilibrium pressure using the ideal gas law (corrected for non-ideality). The skeletal density is taken as the ratio between the sample mass and the volume of solids that make up the porous sample. MICP forces mercury into a porous body by incrementally increasing the pressure applied to the mercury. The size of pores the mercury can access is inversely proportional to the pressure. By monitoring the volume of mercury injected with each increase in pressure, the bulk density can be determined from the sample mass, and the sample volume. The sample volume is the difference between the volume of the sample holder and the volume of the mercury required to surround but not invade the sample. Also the pore size distribution can be determined from the volume of mercury injected at each incremental increase in pressure, and the well known relationship between the pore size and pressure as given by the Washburn equation. The pore volume is determined from the total volume of mercury injected at the highest pressure, and the skeletal density is given by the mass of the sample and the volume of solids that make up the porous medium. The latter quantity is taken as the difference between the volume of the sample holder, and the total amount of mercury required to surround the sample, and fill the accessible pores.

In a non-limiting example, Bulk density, $\rho_B$ is measured by weighing in air and the volume is determined by measuring the displacement of a liquid. Gas permeability is determined using a modified pycnometer technique by analyzing the kinetics of pressure equilibration at a plurality of pressures. With this information, the liquid permeability, k, is inferred from the y-intercept of a linear fit to the correlation with the experimental pressure (See Klinkenberg, "The permeability of porous media to liquids and gases," Drill, Proc. API (1941), 200-213). The skeletal density $\rho_S$ is determined from the equilibrium pressure during the gas permeability measurements utilizing the ideal gas law.

Figure 7:
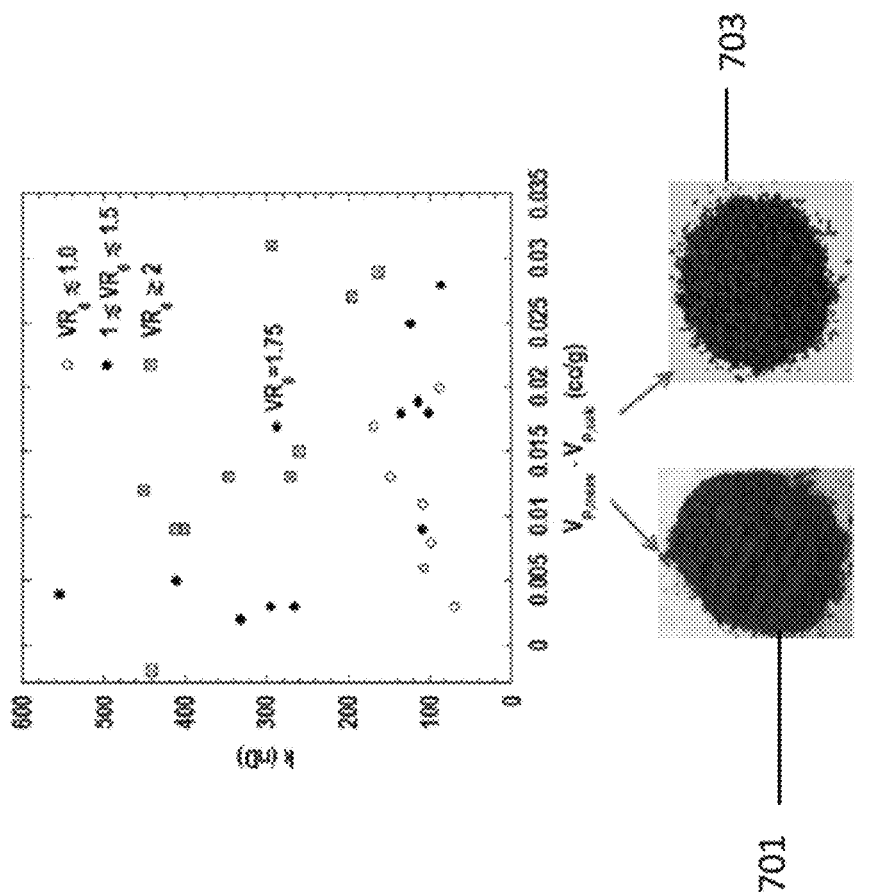
FIG. 7 is a plot of permeability, k, versus the difference between the pore volume measured on two different particle sizes.

FIG. 7 is a plot of permeability k versus the difference between the measured and calculated pore volume. The measured pore volume is measured by nitrogen gas sorption, $V_{P,meas}$, and the calculated pore volume is determined from $\rho_B$ and $\rho_S$, $V_{P,calc}$:

$$V_{P,calc} = \frac{1}{\rho_B} - \frac{1}{\rho_S} \qquad \text{Equation 2}$$

The measurement of $\mu_S$ is on a material that has a characteristic dimension that is at least one order of magnitude greater than that used in the gas sorption experiment, in a non-limiting example $10^{-3}$ m vs. $10^{-4}$ m. The difference in size of the particles can be visually seen in FIG. 7 with the particles (701) used in the measured gas sorption being smaller than the particles (703) used where $\rho_S$ is measured. As a result of this difference, we measure the same or more $V_{P,meas}$ in the gas sorption measurement than we determine from the densities using equation (2). This difference may be attributed to the fact that the gas used in the $\rho_S$ measurement is not able to access all of the porosity. For those samples where $V_{P,meas} > V_{P,calc}$, correlation length ($\chi$) is smaller than the particle size used in the $\rho_S$ measurement ($10^{-3}$). On the other hand, when $V_{P,meas} \approx V_{P,calc}$, correlation length ($\chi$) is greater than or equivalent to the particle size used in the $\rho_S$ measurement ($10^{-4}$). As can be seen in FIG. 7 the mature samples have higher k than the moderate or lower maturity systems over the range in $V_{P,meas}$-$V_{P,calc}$. The exception occurs when $V_{P,meas} \approx V_{P,calc}$, in this case the moderate maturity systems have k that is similar to the highest k of the mature systems. This observation is consistent with the expectation of percolation theory where the highest permeabilities are correlated to the fact that the measured porosity/pore volume does not increase when the particle size is reduced. In any case, k decreases as $V_{P,meas}$ becomes greater than $V_{P,calc}$. A simple permeability model, like the Carmen-Kozeny equation (3) may be used to better understand the relationship between the microstructure and k further:

$$k = \frac{\phi r_H^2}{\kappa} \qquad \text{Equation 3}$$

Where $\emptyset = V_{P\emptyset B}$ is the porosity, $r_H$ is the hydraulic radius, and k is the kozeny constant, which is roughly equivalent to the tortuosity. It has been shown that $r_H$ decreases by a factor of 2 while $V_P$ increases by the same factor over the range of maturity investigated here. According to equation 3 these microstructural variations suggests that if k is constant, k should decrease by a factor of 2 as maturity increases. FIG. 7 indicates that k increases by a factor of 2-4 with increasing maturity. So $\kappa$ drops by as much as factor of 4-8 with an increase in maturity. This observation is also consistent with the predictions of percolation theory. This decrease in $\kappa$ is due to the opening of pores in the organic matter (OM). In terms of reservoir quality, the ideal systems are those with large correlation length ($\chi$) as these systems require less stimulation to fully tap the natural hydrocarbon reserve. At the same times these systems also have more attractive transport properties.

The data shows that the gas sorption measurement sees more pore volume than that determined from the densities. Also, the permeability of moderate and highly mature samples increases as the pore volume determined by the independent technique comes into agreement.

According to further embodiments any combination of the results from gas sorption, and similar results from other characterization techniques e.g., He-pyc or MIP using a plurality of varying particle sizes (0.001-50 mm) will yield information which may be used to determine the correlation length of shale.

As discussed above, the microstructure of mature shale has nanometer sized pores in the kerogen network. Therefore, since the surface area is expected to drop upon removal of organic matter from the shale matrix, a comparison of $A_s$ measured on samples in the native and organic free (via high temperature combustion) states is an alternative means for identifying mature zones (See FIG. 2 combustion data).

In further embodiments the samples are analyzed before and after combustion or bitumen extraction. The shale samples are homogenized and split into two samples, a first and a second sample. The two samples are grinded and then sieved ensuring all material passes through a sieve with 150 μm openings. According to some embodiments the sample sizes are on the order of 1 g. A first sample is then combusted at 450° C. in air for at least 16 hours to remove organic matter or subjected to solvent reflux for several days to remove bitumen. In order to run gas sorption analysis the first sample is dried. A second sample is placed in a vacuum oven overnight. The total organic content (TOC) is estimated in the first sample from mass loss due to combustion or bitumen removal. The samples are then loaded into a clean sample tube and the mass of each of the samples is noted. Gas sorption analysis is then performed on both samples noting the $V_A$ of $P/P_0$ in the pressure range $0.01<P/P_0<0.995$, including a point at the upper bound. The surface area ($A_s$) is determined by the BET method on both samples and the results are compared. If the surface area ($A_s$) is reduced by 200 m$^2$/g/TOC after combustion the sample may be considered mature (see FIG. 3—filled symbols). If the surface area ($A_s$) increases markedly upon bitumen extraction, the sample may be considered moderately mature (see FIG. 3—open symbols). The gas sorption data from the native-state sample is analyzed using the t-plot method to check for microporosity, if the sample contains micropores, the sample is mature. The pore volume is determined from the volume of adsorbed gas ($V_A$) at the highest pressure and the pore volume available to free gas ($V_F$). ($V_F$) may also be determined as indicated above.

Figure 8:
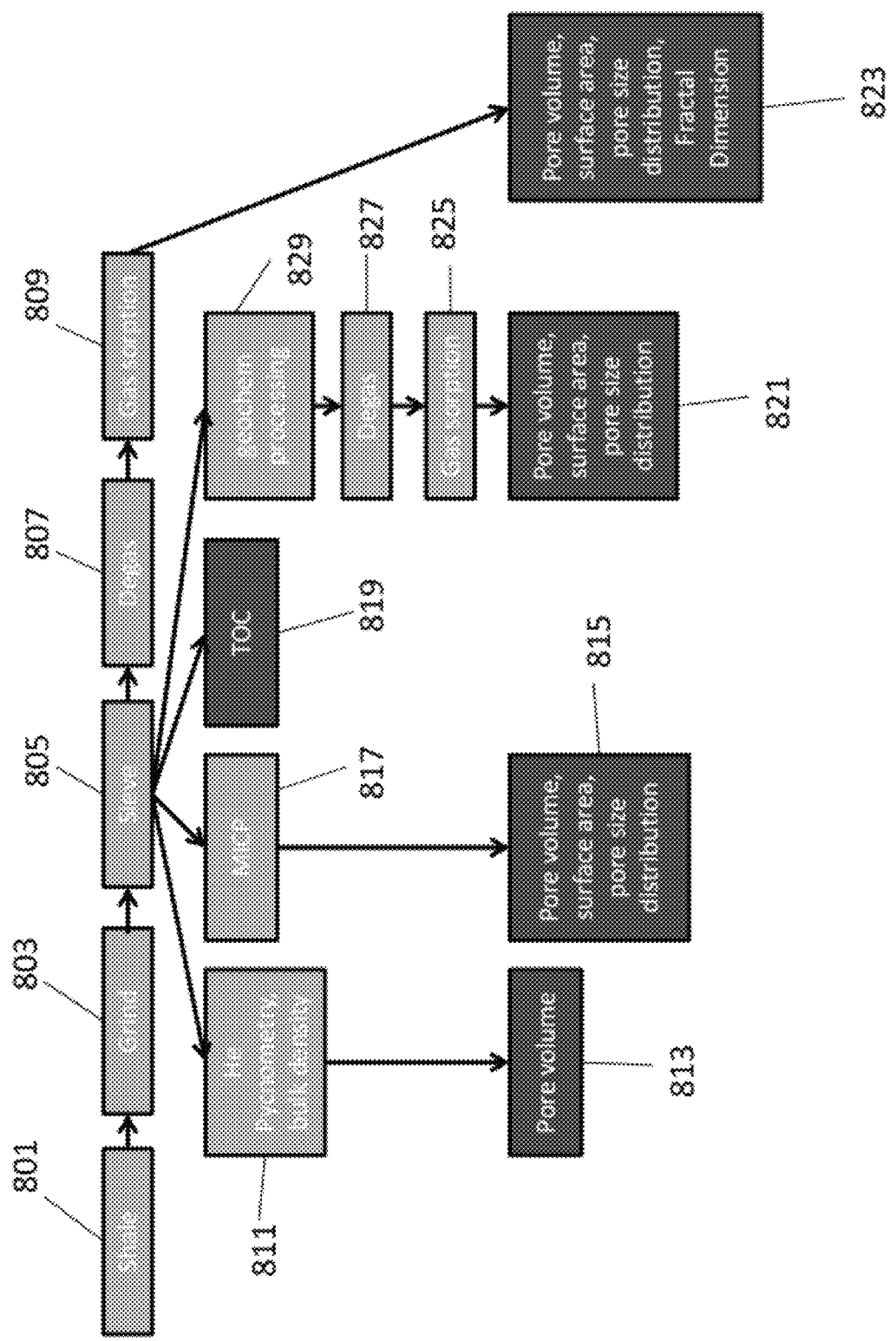
FIG. 8 is a flow chart of an embodiment of the subject disclosure.

FIG. 8 depicts a flow chart of embodiments of the subject disclosure. In an embodiment the shale sample (801) is grinded (803) and then sieved (805) ensuring all material passes through a sieve with a predefined opening, in a non-limiting example the opening is 150 µm. The shale sample (801) is then degassed (807) in preparation for gas sorption analysis (809). From gas sorption analysis (809) a plurality of microstructural characteristics (823) are determined which include pore volume, surface area, pore size distribution and fractal dimension and correlation length or relative pore connectivity.

In a further embodiment the shale sample (801) is grinded (803) and then sieved (805) and the sample is then analyzed using helium pycnometry (He-pyc) and bulk density. The pore volume (813) can be determined with this approach.

In a further embodiment the shale sample (801) is grinded (803) and then sieved (805) and the sample is then analyzed using MICP (817). From MICP (817) a plurality of physical and microstructural characteristics (823) are determined which include bulk density, skeletal density, pore volume, surface area and pore size distribution.

The pore volume or porosity may also be measured on varying sized particles in the rock sample using any of the techniques disclosed or any techniques known to those skilled in the art for measuring the pore volume and the porosity in a rock sample and the results are compared to determine the correlation length or relative pore connectivity in the system.

Comparing any output 813, 815, 819, 821 or 823 yields information regarding pore connectivity, more specifically the dimension over which the porosity is connected in 3D. When mercury intrusion porosimetry (MICP) is used the size of pores controlling transport and the pore morphology may also be determined.

Whereas many alterations and modifications of the present invention will no doubt become apparent to a person of ordinary skill in the art after having read the foregoing description, it is to be understood that the particular embodiments shown and described by way of illustration are in no way intended to be considered limiting. Further, the invention has been described with reference to particular preferred embodiments, but variations within the spirit and scope of the invention will occur to those skilled in the art. It is noted that the foregoing examples have been provided merely for the purpose of explanation and are in no way to be construed as limiting of the present invention. While the present invention has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A method of analyzing rock samples from an unconventional hydrocarbon reservoir comprising:
    performing gas sorption on a sample of rock from the unconventional hydrocarbon reservoir; and
    determining at least one characteristic associated with the sample based at least in part on the gas sorption, wherein the at least one characteristic is thermal maturity calculated from a fractal dimension of the sample.

2. A method of analyzing rock samples from an unconventional hydrocarbon reservoir comprising:
    performing gas sorption on a sample of rock from the unconventional hydrocarbon reservoir; and
    determining at least one characteristic associated with the sample based at least in part on the gas sorption, wherein the at least one characteristic is thermal maturity calculated from a surface area of the sample.

* * * * *